United States Patent
Chen et al.

(10) Patent No.: US 12,252,551 B2
(45) Date of Patent: Mar. 18, 2025

(54) METHODS AND KITS FOR DIAGNOSING AND/OR TREATING PERIPHERAL NEUROPATHY

(71) Applicant: Academia Sinica, Taipei (TW)

(72) Inventors: Chih-Cheng Chen, Taipei (TW); Yu-Chia Chuang, Taipei (TW)

(73) Assignee: Academia Sinica, Taipei (TW)

( * ) Notice: Subject to any disclaimer, the term of this patent is extended or adjusted under 35 U.S.C. 154(b) by 1227 days.

(21) Appl. No.: 16/978,278

(22) PCT Filed: Mar. 5, 2019

(86) PCT No.: PCT/US2019/020638
§ 371 (c)(1),
(2) Date: Sep. 4, 2020

(87) PCT Pub. No.: WO2019/173258
PCT Pub. Date: Sep. 12, 2019

(65) Prior Publication Data
US 2021/0355207 A1    Nov. 18, 2021

Related U.S. Application Data

(60) Provisional application No. 62/638,338, filed on Mar. 5, 2018.

(51) Int. Cl.
| | |
|---|---|
| C07K 16/18 | (2006.01) |
| A61K 31/135 | (2006.01) |
| A61K 31/195 | (2006.01) |
| A61K 31/485 | (2006.01) |
| A61K 45/06 | (2006.01) |
| A61P 25/00 | (2006.01) |
| C07K 16/28 | (2006.01) |
| C07K 16/44 | (2006.01) |
| A61K 39/00 | (2006.01) |

(52) U.S. Cl.
CPC ............ *C07K 16/44* (2013.01); *A61K 31/135* (2013.01); *A61K 31/195* (2013.01); *A61K 31/485* (2013.01); *A61K 45/06* (2013.01); *A61P 25/00* (2018.01); *C07K 16/28* (2013.01); *A61K 2039/505* (2013.01)

(58) Field of Classification Search
None
See application file for complete search history.

(56) References Cited

U.S. PATENT DOCUMENTS

2018/0193414 A1* 7/2018 Greenberg .............. A61P 25/16

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Johnson and Wu (Methods in Molecular Biology, Antibody Engineering: Methods and Protocols, vol. 248, p. 11-25, 2004) (Year: 2004).*
Rudikoff et al. (Proceedings of the National Academy of Sciences USA, vol. 79, p. 1979-1983, 1982) (Year: 1982).*

* cited by examiner

*Primary Examiner* — Michael Allen
(74) *Attorney, Agent, or Firm* — NZ Carr Law Office

(57) ABSTRACT

Disclosed herein are method and/or kit for rendering a diagnosis on whether a subject is suffering from peripheral neuropathy pain. The method comprises detecting the presence of advillin in a biological sample by forming an immune complex between advillin and a monoclonal antibody specifically binds thereto. Also disclosed herein is a method of treating a subject suffering from peripheral neuropathy pain.

3 Claims, 5 Drawing Sheets
Specification includes a Sequence Listing.

A

B

SEQUENCE LISTING

```
<160> NUMBER OF SEQ ID NOS: 37

<210> SEQ ID NO 1
<211> LENGTH: 22
<212> TYPE: PRT
<213> ORGANISM: Artificial Sequence
<220> FEATURE:
<223> OTHER INFORMATION: Synthetic

<400> SEQUENCE: 1

Lys Asn Gln Asn Gln Glu Leu Pro Glu Asp Val Asn Pro Ala Lys Lys
1               5                   10                  15

Glu Asn Tyr Leu Ser Glu
            20

<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Leu Lys Asn Gln Asn Gln Glu Leu Pro Glu Asp Val Asn Pro Ala Lys
1               5                   10                  15

Lys Glu Asn Tyr Leu Ser Glu Gln Asp
            20                  25

<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Asp Gly Glu Pro Lys Tyr Tyr Pro Val Glu Val Leu Lys Gly Gln Asn
1               5                   10                  15

Gln Glu Leu

<210> SEQ ID NO 4
<211> LENGTH: 57
<212> TYPE: DNA
<213> ORGANISM: Artificial Sequence
<220> FEATURE:
<223> OTHER INFORMATION: Synthetic

<400> SEQUENCE: 4
```

```
atggacttga gactgagctg cgcttttatt attgttcttt taaaaggggt ccagagt        57
```

<210> SEQ ID NO 5
<211> LENGTH: 90
<212> TYPE: DNA
<213> ORGANISM: Artificial Sequence
<220> FEATURE:
<223> OTHER INFORMATION: Synthetic

<400> SEQUENCE: 5

```
gaagtgaagc ttgaggagtc aggaggaggc ttggtgcaac ctggaggatc cttgaaactc        60
tcctgtgtag cctctggatt tgctttcagt                                         90
```

<210> SEQ ID NO 6
<211> LENGTH: 15
<212> TYPE: DNA
<213> ORGANISM: Artificial Sequence
<220> FEATURE:
<223> OTHER INFORMATION: Synthetic

<400> SEQUENCE: 6

```
aattcctgga tgtct                                                         15
```

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7

```
tgggtccgcc agtctccaga gaagggactt gagtgggttg ct                           42
```

<210> SEQ ID NO 8
<211> LENGTH: 57
<212> TYPE: DNA
<213> ORGANISM: Artificial Sequence
<220> FEATURE:
<223> OTHER INFORMATION: Synthetic

<400> SEQUENCE: 8

```
gaaattagat tgaaatctga taattatgca tcacattatg cggagtctgt gaaaggg           57
```

<210> SEQ ID NO 9
<211> LENGTH: 96
<212> TYPE: DNA
<213> ORGANISM: Artificial Sequence
<220> FEATURE:
<223> OTHER INFORMATION: Synthetic

<400> SEQUENCE: 9

```
aggttcacca tctcaagaga tgattccaaa agtcgtctct acctgcaaat gaatgcctta        60
agagctgaag acactggaat ttattattgt tcagat                                  96
```

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10

```
gggacctggt ttacttac                                                      18
```

```
<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
tggggccaag ggactctggt cactgtctct aca                          33

<210> SEQ ID NO 12
<211> LENGTH: 60
<212> TYPE: DNA
<213> ORGANISM: Artificial Sequence
<220> FEATURE:
<223> OTHER INFORMATION: Synthetic

<400> SEQUENCE: 12
atggattcac aggcccaggt tcttatgtta ctgctgctat gggtatctgg tacctgtggg    60

<210> SEQ ID NO 13
<211> LENGTH: 69
<212> TYPE: DNA
<213> ORGANISM: Artificial Sequence
<220> FEATURE:
<223> OTHER INFORMATION: Synthetic

<400> SEQUENCE: 13
gacattgtga tgtcacagtc tccatcctcc ctagctgtgt cagttggaga gaaggttact    60
atgaactgc                                                            69

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
aagtccagtc agagcctttt atatcgtgcc aatcaaaaga actacttggc c              51

<210> SEQ ID NO 15
<211> LENGTH: 45
<212> TYPE: DNA
<213> ORGANISM: Artificial Sequence
<220> FEATURE:
<223> OTHER INFORMATION: Synthetic

<400> SEQUENCE: 15
tggtaccagc agaaaccagg gcagtctcct aaactgctga tttac                     45

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
tgggcatcca ctagggaatc t                                               21

<210> SEQ ID NO 17
<211> LENGTH: 96
<212> TYPE: DNA
<213> ORGANISM: Artificial Sequence
```

```
<220> FEATURE:
<223> OTHER INFORMATION: Synthetic

<400> SEQUENCE: 17
ggggtccctg atcgcttcac aggcagtgga tctgggacag atttcactct caccatcagc    60
agtgtgaagg ctgaagacct ggcagtttat tactgt                              96

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
cagcaatatt atagccatcc attcacg                                        27

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
ttcggctcgg ggacaaagtt gaaataaaa                                      30

<210> SEQ ID NO 20
<211> LENGTH: 19
<212> TYPE: PRT
<213> ORGANISM: Artificial Sequence
<220> FEATURE:
<223> OTHER INFORMATION: Synthetic

<400> SEQUENCE: 20

Met Asp Leu Arg Leu Ser Cys Ala Phe Ile Ile Val Leu Leu Lys Gly
1               5                   10                  15

Val Gln Ser

<210> SEQ ID NO 21
<211> LENGTH: 30
<212> TYPE: PRT
<213> ORGANISM: Artificial Sequence
<220> FEATURE:
<223> OTHER INFORMATION: Synthetic

<400> SEQUENCE: 21

Glu Val Lys Leu Glu Glu Ser Gly Gly Gly Leu Val Gln Pro Gly Gly
1               5                   10                  15

Ser Leu Lys Leu Ser Cys Val Ala Ser Gly Phe Ala Phe Ser
            20                  25                  30

<210> SEQ ID NO 22
<211> LENGTH: 5
<212> TYPE: PRT
<213> ORGANISM: Artificial Sequence
<220> FEATURE:
<223> OTHER INFORMATION: Synthetic

<400> SEQUENCE: 22

Asn Ser Trp Met Ser
1               5

<210> SEQ ID NO 23
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 23

Trp Val Arg Gln Ser Pro Glu Lys Gly Leu Glu Trp Val Ala
1               5                   10

<210> SEQ ID NO 24
<211> LENGTH: 19
<212> TYPE: PRT
<213> ORGANISM: Artificial Sequence
<220> FEATURE:
<223> OTHER INFORMATION: Synthetic

<400> SEQUENCE: 24

Glu Ile Arg Leu Lys Ser Asp Asn Tyr Ala Ser His Tyr Ala Glu Ser
1               5                   10                  15

Val Lys Gly

<210> SEQ ID NO 25
<211> LENGTH: 32
<212> TYPE: PRT
<213> ORGANISM: Artificial Sequence
<220> FEATURE:
<223> OTHER INFORMATION: Synthetic

<400> SEQUENCE: 25

Arg Phe Thr Ile Ser Arg Asp Asp Ser Lys Ser Arg Leu Tyr Leu Gln
1               5                   10                  15

Met Asn Ala Leu Arg Ala Glu Asp Thr Gly Ile Tyr Tyr Cys Ser Asp
                20                  25                  30

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Gly Thr Trp Phe Thr Tyr
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic

<400> SEQUENCE: 27

Trp Gly Gln Gly Thr Leu Val Thr Val Ser Thr
1               5                   10

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

Met Asp Ser Gln Ala Gln Val Leu Met Leu Leu Leu Leu Trp Val Ser
```

-continued

```
                1               5                  10                 15
Gly Thr Cys Gly
            20

<210> SEQ ID NO 29
<211> LENGTH: 23
<212> TYPE: PRT
<213> ORGANISM: Artificial Sequence
<220> FEATURE:
<223> OTHER INFORMATION: Synthetic

<400> SEQUENCE: 29

Asp Ile Val Met Ser Gln Ser Pro Ser Ser Leu Ala Val Ser Val Gly
1               5                   10                  15

Glu Lys Val Thr Met Asn Cys
            20

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Lys Ser Ser Gln Ser Leu Leu Tyr Arg Ala Asn Gln Lys Asn Tyr Leu
1               5                   10                  15

Ala

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Trp Tyr Gln Gln Lys Pro Gly Gln Ser Pro Lys Leu Leu Ile Tyr
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Trp Ala Ser Thr Arg Glu Ser
1               5

<210> SEQ ID NO 33
<211> LENGTH: 32
<212> TYPE: PRT
<213> ORGANISM: Artificial Sequence
<220> FEATURE:
<223> OTHER INFORMATION: Synthetic

<400> SEQUENCE: 33

Gly Val Pro Asp Arg Phe Thr Gly Ser Gly Ser Gly Thr Asp Phe Thr
1               5                   10                  15

Leu Thr Ile Ser Ser Val Lys Ala Glu Asp Leu Ala Val Tyr Tyr Cys
            20                  25                  30
```

```
<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln Gln Tyr Tyr Ser His Pro Phe Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Phe Gly Ser Gly Thr Lys Leu Lys Ile Lys
1               5                   10

<210> SEQ ID NO 36
<211> LENGTH: 31
<212> TYPE: DNA
<213> ORGANISM: Artificial Sequence
<220> FEATURE:
<223> OTHER INFORMATION: Synthetic

<400> SEQUENCE: 36
gagggatcca tgcctctgac cagtgccttc a                              31

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
cgctctagac ttgctttaga aaagcccctt                                30
```

METHODS AND KITS FOR DIAGNOSING AND/OR TREATING PERIPHERAL NEUROPATHY

CROSS REFERENCE TO RELATED APPLICATION

This application is a U.S. National Stage Filing under 35 U.S.C. 371 from International Patent Application Serial No. PCT/US2019/020638, entitled "METHODS AND KITS FOR DIAGNOSING AND/OR TREATING PERIPHERAL NEUROPATHY," filed on Mar. 5, 2019, and published on Sep. 12, 2019, the disclosure of which are incorporated by reference herein in their entireties.

BACKGROUND OF THE INVENTION

1. Field of the Invention

The present disclosure relates in general, to the field of peripheral neuropathy; more specifically, to the field of diagnosis and treatments of peripheral neuropathy.

2. Description of Related Art

A subject exhibits a disorder of one or more peripheral nerves is said to suffer from a peripheral neuropathy. Peripheral nerves extend beyond the brain and spinal cord into tissues that lie outside the central nervous system to provide a bidirectional communication network. They serve as conduits of impulses from the brain and spinal cord to the rest of the body: for example, motor neurons carry signals to direct movement. Peripheral nerves are also capable of transmitting sensory information gathered by specialized receptors to the brain. In short, peripheral nerves provide the connection between brain, body, and environment, and serve to coordinate the relationship between an organism's brain and the outside world.

Numerous varieties of peripheral neuropathy exist. Some are common, others are extremely rare. The etiology of certain peripheral neuropathies is well understood but some remain a mystery. Many neuropathies have been classified into particular syndromes. Each syndrome is associated with its own set of clinical symptoms and signs, prognosis, and treatment options. It is extremely important to be able to match a particular patient with the syndrome that corresponds to his or her clinical condition. Such matching, like a road map, permits the physician to choose a course of treatment and to counsel the patient as to prognosis. Often the identification of a syndrome alerts the physician to another medical condition associated with the patient's peripheral neuropathy, which requires a particular course of treatment and carries its own prognosis. Accordingly, the ability to make a correct and precise diagnosis is exceedingly important in the management of a patient suffering from a peripheral neuropathy. Making the correct diagnosis may, however, be difficult. In the past, such diagnosis has depended upon an analysis of the patient's symptoms and an extremely detailed physical examination. To further complicate matters, many peripheral neuropathy syndromes have not yet been fully characterized.

In view of the foregoing, there exists in this art a need of a novel marker useful for rendering diagnosis on a subject suffering from peripheral neuropathy.

SUMMARY

The present disclosure is based, at least in part, unexpected discovery that advillin, a sensory neuron-specific protein, may serve as a biomarker for the diagnosis of peripheral neuropathy. To this purpose, monoclonal human antibody against advillin is developed for use in the methods and kits for detecting advillin from a biological sample of a subject suspected of having peripheral neuropathy: as well as in methods for rendering diagnosis on the subject.

Accordingly, it is the first aspect of the present disclosure to provide a monoclonal antibody specifically binds to an epitope of advillin.

According to embodiments of the present disclosure, the monoclonal antibody is produced by the hybridoma YCC-S1.

According to embodiments of the present disclosure, the monoclonal antibody is an IgG or an IgM.

The second aspect of the present disclosure is directed to a method of making a diagnosis on whether a subject is suffering from peripheral neuropathy pain. The diagnosis is made based on a biological sample of the subject, and the method includes steps of:

detecting the presence of a complex formed between advillin in the biological sample and the monoclonal antibody of the present disclosure in an immunological assay;

wherein the formation of the complex is an indication that the subject suffers from peripheral neuropathy pain.

According to embodiments of the present disclosure, the monoclonal antibody is an IgG or an IgM.

According to embodiments of the present disclosure, the biological sample is cerebrospinal fluid, peritoneal fluid, blood, serum, or plasma.

According to embodiments of the present disclosure, the peripheral neuropathy pain is resulted from damage in sensory neurons, preferably, the sensory neurons specifically bind to isolectin B4, calcitonin gene-related peptide (CGRP), substance P, or neurofilament 200.

According to embodiments of the present disclosure, the immunological assay is western blot analysis, enzyme linked immunosorbent assay (ELISA), radio immunoassay (RIA), immunohistochemistry (IHC) assay, or immunocytochemistry (ICC) assay.

The third aspect of the present disclosure is directed to a method for treating a subject having a peripheral neuropathy pain. The method comprises:

(a) obtaining a biological sample of the subject;
(b) mixing the biological sample with the monoclonal antibody of the present disclosure so as to react advillin in the biological sample with the monoclonal antibody thereby forming a complex therebetween in an immunoassay; and
(c) administering an effective amount of a therapeutic agent to the subject to ameliorate the peripheral neuropathy pain, in which the therapeutic agent is a pain reliever, an anti-seizure agent, or an anti-depressant.

According to embodiments of the present disclosure, in the step (a), the biological sample may be cerebrospinal fluid, peritoneal fluid, blood, serum, plasma, or tissue biopsy.

According to embodiments of the present disclosure, in the step (b), the immunological assay may be western blot analysis, enzyme linked immunosorbent assay (ELISA), radio immunoassay (RIA), immunohistochemistry (IHC) assay, or immunocytochemistry (ICC) assay.

According to embodiments of the present disclosure, the pain reliever may be a nonsteroidal anti-inflammatory drug (NSAID), opioid or oxycodone. Examples of the NSAID suitable for use in the present method include, but are not limited to, aspirin, ibuprofen, dexibuprofen, naproxen, fenoprofen, dexketoprofen, flurbiprofen, loxoprofen, indomethacin, tolmetin, sulindac, etodolac, ketorolac, diclofenac, acelofenac, prioxicam, meloxicam, tenoxicam, droxicam, lornoxicam, isoxicam, phenylbutazone, mefenamic acid, meclofenamic acid, flfenamic acid, and tolfenamic acid.

According to embodiments of the present disclosure, the anti-seizure agent may be gabapentin or pregabalin.

According to embodiments of the present disclosure, the anti-depressant may be amitriptyline, doxepin or nortriptyline.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where.

DESCRIPTION

Figure 1:
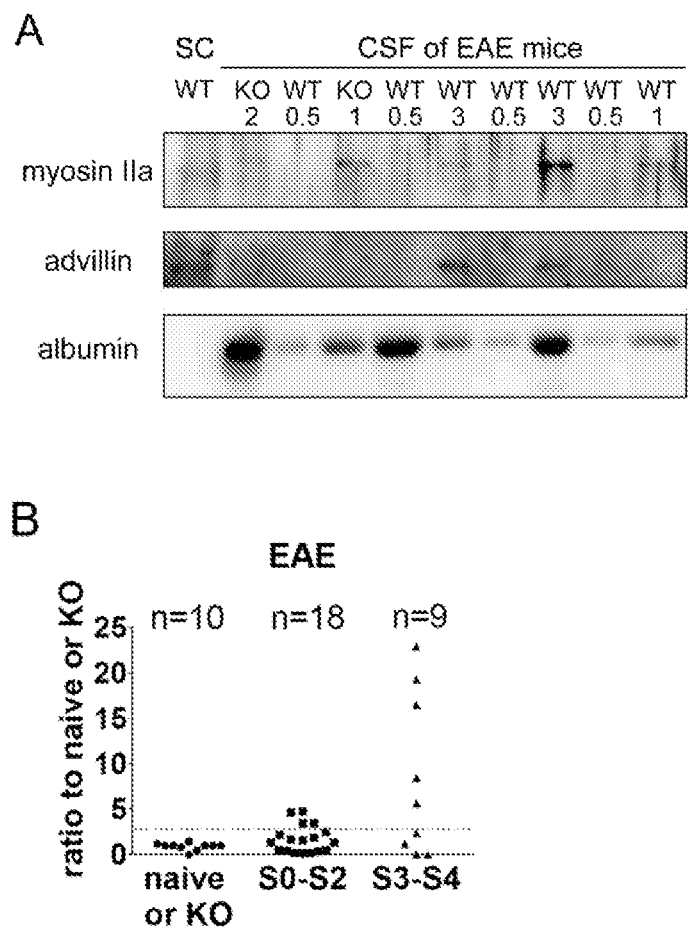
FIG. 1 Western blot analysis of advillin in CSF of EAE mice. (A) Representative western blot analysis of advillin protein levels in cerebrospinal fluid (CSF) of experimental autoimmune encephalomyelitis (EAE) mice. CSF samples were collected from EAE mice in the recovery phase. Each lane was loaded with 4 μl CSF sample or 10 μg WT spinal cord lysates as a positive control. Albumin was a loading control. The number below the genotype indicates the EAE clinical score on the day of CSF collection. Myosin IIa is an advillin-interacting protein. (B) Quantification of advillin expression in CSF samples. The dotted line is the threshold level (mean of negative samples+5×SD) to define positive advillin expression.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

The term "antibody" or "antibodies" is used in the broadest sense and specifically covers monoclonal antibodies, polyclonal antibodies, multispecific antibodies (e.g., bi-specific antibodies), and antibody fragments so long as they exhibit the desired biological activity, that is, to specifically bind to an antigen when it preferentially recognizes its target antigen in a complex mixture of proteins and/or other molecules. The antibody according to this disclosure may be any type (e.g., IgG, IgM, IgD, IgE, IgA and IgY) or class (e.g., IgG1, IgG2, IgG3, IgG4, IgA1 and IgA2) or subclasses of immunoglobulin molecules.

The term "monoclonal antibody" as used herein refers to an antibody obtained from a population of homogeneous antibodies, and is not to be constructed as requiring production of the antibody by any particular method. In contrast to polyclonal antibodies which typically include different antibodies directed to different epitopes, each monoclonal antibody is directed against a single determinant (i.e., epitope)

on the antigen. Monoclonal antibodies are typically produced by fusing a normally short-lived, antibody-producing B cell to a fast-growing cell, such as an immortal cell. The resulting hybrid cell, or hybridoma, multiplies rapidly, creating a clone that produces large quantities of the antibody. Alternatively, monoclonal antibodies may also be produced by recombinant DNA methods, in which a portion of the heavy and/or light chain is identical with or homologous to corresponding sequences in antibodies derived from a particular species or belonging to a antibody class or subclass, while the remainder of the chain identical with or homologous to corresponding sequences in antibodies derived from another species or belonging to another antibody class or subclass, as well as fragments of such antibodies, as long as they exhibit the desired biological activity.

The term "subject" or "patient" refers to an animal including the human species that may be diagnosed with the present invention. The term "subject" or "patient" intended to refer to both the male and female gender unless one gender is specifically indicated. Accordingly, the term "subject" or "patient" comprises any mammal which may benefit from the treatment method of the present disclosure.

The term "identical" or "percent identity" as used herein refers to two or more sequences or subsequences that are the same or have a specified percentage of amino acid residues that are the same, when compared and aligned for maximum correspondence. To determine the percent identity, the sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=(number of identical positions/total number of positions)*100). In certain embodiments, the two sequences are of the same length. Thus, 100% identity means, for example, that upon comparing 20 sequential amino acid residues in two different molecules, both 20 residues in the two different molecules are identical.

The singular forms "a," "and," and "the" are used herein to include plural referents unless the context clearly dictates otherwise.

1. Advillin Monoclonal Antibodies

The practices of this invention are hereinafter described in detail with respect to monoclonal antibodies against advillin, hybridoma cells producing the same, and their uses in detecting advillin that might be present in a biological sample, such as, cerebrospinal fluid (CSF), peritoneal fluid, blood, serum, plasma or a tissue biopsy (e.g., skin) of a subject, so as to determine whether the host of the biological sample is suffering from peripheral neuropathy pain.

According to one aspect of the present disclosure, monoclonal antibody that specifically binds to human advillin is provided.

To produce the desired monoclonal antibodies, animals such as mice, rats or rabbits are first immunized with a synthetic peptide conjugated with ovalbumin at a suitable dose. In one example, the synthetic peptide has the amino acid sequence of KNQNQELPEDVNPAKKENYLSE (SEQ ID NO: 1) that corresponds to the headpiece domain of human advillin. In another example, the synthetic peptide has the amino acid sequence of DGEPKYYPVEVLKGQNQEL (SEQ ID NO: 3) that corresponds to the headpiece domain of mouse advillin. Generally, adjuvant and the antigen solution are mixed together when immunizing the animals. Examples of adjuvants useful for this invention include complete Freund's adjuvant (CFA), incomplete Freund's adjuvant (IFA), and aluminum hydroxide adjuvant. Immunization is generally carried out mainly by intravenous, subcutaneous, intraperitoneal or intramuscular injection of the antigen. The immunization interval is not particularly limited. Immunization may be carried out at intervals of several days to several weeks, preferably 2 to 3 weeks, for 1 to 10 times, preferably 2 to 5 times. Once antibody titers reaches 2 or more in the absorbance level as the result of immunization, the animals are left for 2 to 6 months, preferably 4 to 6 months, more preferably 6 months, until the antibody titers have decreased to 0.05-1, preferably 0.05-0.5, more preferably 0.05, in the absorbance level.

Then, re-immunization is carried out for a plurality of times, preferably 2 to 5 times, at intervals of several weeks. Several days, preferably 3 to 5 days, after the final immunization, splenic cells and regional lymph nodes are removed. Blood samples are taken regularly after immunization and subject to centrifugation to separate sera. The resultant sera are then subjected to measurement of antibody titers by any suitable method, which includes, and is not limited to, western blot analysis, enzyme linked immunosorbent assay (ELISA), radio immunoassay (RIA), immunohistochemistry (IHC) assay, or immunocytochemistry (ICC) assay. In one preferred example, antibody titers are measured by ELISA. Then, final immunization is given to those animals showing high antibody titers to advillin.

Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer of ammonium chloride and Tris may be prepared and used.

The thus prepared antibody-producing cells are immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should not survive in HAT selection medium, which contains hypoxanthine, thymidine and aminopterin, and should survive there only when fused with antibody-producing cells. Examples of myeloma cells include, but are not limited to, mouse myeloma cell line (such as myeloma FO cells) and human myeloma cell line (such as Karpas 707H).

Cell fusion is usually carried out by mixing splenic cells or lymph node cells with a commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electroporation. After the fusion, the resultant cells are then diluted and cultured in HAT medium. To the purpose of producing monoclonal antibodies, aminopterin in the medium blocks the de novo pathway. Hence, unfused myeloma cells die, as they cannot produce nucleotides by the de novo or salvage pathway. Unfused B cells die as they have a short lifespan. In this way, only the B cell-myeloma hybrids (i.e., hybridomas of onterest) survive. These cells produce antibodies (a property of B cells) and are immortal (a property of myeloma cells). The incubated medium is then diluted into multiwell plates to such an extent that each well contains only 1 cell. Then the supernatant in each well is collected and examined for the presence or absence of antibody titers to advillin. As a method of confirmation, ELISA, EIA or RIA may be used. Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to advillin are selected, and are proliferated to some extent to establish hybridomas.

According to preferred embodiment of the present disclosure, one hybridoma was selected and is named "YCC-S1." The selected hybridoma could produce monoclonal antibodies that specifically bind to exogeneous expressed human advillins in 293T cells.

The thus produced monoclonal antibodies may be isolated or prepared by any known method. For example, antibodies may be prepared from cultured supernatant obtained by culturing hybridomas in a medium with low serum concentration.

Alternatively, hybridomas may be injected into abdominal cavities of animals and the resultant abdominal dropsies are collected to prepare antibodies. Antibodies may be purified or isolated by methods that employ affinity column, gel filtration chromatography, ion exchange chromatography or the like. Any of these known methods may be appropriately selected or used in combination.

According to one embodiment of the present disclosure, the monoclonal antibody produced by the selected strain specifically binds to human advillin. The thus produced monoclonal antibody is an IgG and is termed "hAvil" hereafter. The present hAvil is characterized in having a heavy chain and a light chain. Each heavy chain or light chain comprises a variable region constituted by complementarity-determining region (CDR) 1, CDR2, and CDR3. The present hAvil comprises a heavy chain variable region comprising the amino acid sequence of SEQ ID NOs: 22, 24, and 26; a light chain variable region comprising the amino acid sequence of SEQ ID NOs: 30, 32, and 34.

Alternatively, the anti-advillin monoclonal antibodies may be produced by DNA cloning. Based on the amino acid sequence of the hAvil, DNA encoding hAvil may be easily isolated and sequenced by use of conventional procedures, such as using oligonucleotide probes that are capable of binding specifically to genes encoding the heavy and light chains of the monoclonal antibodies. The hybridoma cells (e.g., YCC-S1 hybridoma) serve as a preferred source of such DNA. Once isolated, the DNA may be placed into expression vectors, which are then transfected into host cells such as *E. coli* cells, simian COS cells or Chinese hamster ovary (CHO) cells or myeloma cells that do not produce immunoglobulin proteins, to synthesize the desired monoclonal antibodies in the recombinant host cells.

According to embodiments of the present disclosure, the nucleic acid encoding the heavy chain variable region of the anti-advillin monoclonal antibody comprises polynucleotide sequences of SEQ ID NOs: 6, 8, and 10 respectively encoding the amino acid sequences of CDR1, CDR2, and CDR3 of the heavy chain. The nucleic acid encoding the light chain variable region of the anti-advillin monoclonal antibody comprises polynucleotide sequences of SEQ ID NOs: 14, 16, and 18 respectively encoding the amino acid sequences of the CDR1, CDR2, and CDR3 of the light chain.

The monoclonal antibodies thus produced and the DNA encoding such antibodies can then be used to produce chimeric antibodies, humanized antibodies and/or antibody fragments derived thereof.

2. Methods and/or Kits for Diagnosing Peripheral Neuropathy Pain

Also within the scope of the present disclosure is a method for detecting and/or making a diagnosis on whether a subject is suffering from peripheral neuropathy pain.

According to some embodiments of the present disclosure, advillin is present in the cerebrospinal fluid of experimental autoimmune encephalomyelitis (EAE) mice, which are mice that model multiple sclerosis and show severe peripheral neuropathy associated with IB4' sensory neurons (Wang et al., 2017: *Scientific Reports* 7:42304). According to other embodiments of the present disclosure, advillin is also present in oxaliplatin treated mice, which are mice that model chemotherapeutic agent-induced peripheral neuropathic pain, which is associated with IB4$^+$ sensory neurons. According to further embodiment, advillin is also present in mice treated with chronic constriction of sciatic nerve, which are mice that model local neuropathy associated with IB4+ sensory neurons (Casals-Diaz et al., 2009; *Exp Neurol* 217:84-95). Thus, advillin may serve as a biomarker for rendering diagnosis on whether a subject has peripheral neuropathy pain.

Accordingly, the present disclosure also aims at providing a method of making a diagnosis on whether a subject is suffering from peripheral neuropathy pain. The diagnosis is made based on a biological sample obtain from the subject, and the method comprises: detecting the presence of a complex formed between the advillin in the biological sample and the monoclonal antibody of the present disclosure in an immunological assay: wherein, the formation of the complex is an indication that the subject suffers from peripheral neuropathy pain.

According to one embodiment of this invention, it is possible to detect advillin by reacting the monoclonal antibody described above with a biological sample thereby forming a complex that may be identified by immunoassay, which includes but is not limited to, western blot analysis, enzyme linked immunosorbent assay (ELISA), radio immunoassay (RIA), immunohistochemistry (IHC) assay, or immunocytochemistry (ICC) assay. The measured result may then be used as an indicator to determine whether the host of the biological sample is suffering from peripheral neuropathy pain.

For this purpose, biological sample are taken from subjects suspicious of having peripheral neuropathy pain. The biological sample may be any of a whole blood sample, a plasma sample, a serum sample, an ascites (or peritoneal fluid), or a cerebrospinal fluid (CSF) sample, purified or filtered forms thereof, or a skin biopsy. From the view point of early detection, blood, serum, plasma, ascites, CSF, or skin biopsy sample is preferred. The thus prepared biological samples are then reacted with the monoclonal antibodies of this disclosure. Measurement of peripheral neuropathy pain or measurement of advillin level in the biological sample may be performed by conventional ELISA or dot-blot analysis.

According to another embodiment of the present disclosure, it is possible to use the monoclonal antibody against advillin in a detection kit or as a reagent for advillin detection.

The inventors have thus contemplated an advillin detection kit, which is capable of measuring the level of advillin in a biological sample with high sensitivity. The kit of the present invention includes at least, the monoclonal antibodies of the present disclosure; at least one agent suitable for detecting the binding of hAvil with advillin in the biological sample of the subject; and a legend associated with the kit and indicating how to use the kit.

The biological sample described herein includes, but is not limited to, a whole blood sample, a serum sample, a plasma sample, a CSF sample, a peritoneal fluid sample (or ascites), and purified or filtered forms thereof, or skin biopsy. The components included in the kits are: a container: the monoclonal antibodies hAvil; reagents for detecting a biological sample; and a legend associated with the container and indicating how to use the monoclonal antibodies for detecting advillin in the biological sample. The legend may be in a form of pamphlet, CD, VCD, DVD or a software application. The kit may further comprise a negative control that indicates the normal level of advillin in a subject.

3. Methods for Treating Peripheral Neuropathy Pain

Also within the scope of the present disclosure is a method for treating a subject suffering from peripheral neuropathy pain. As indicated above, advillin may serve as a biomarker for rendering diagnosis on whether a subject has peripheral neuropathy pain. Accordingly, once the subject is diagnosed to have peripheral neuropathy pain, treatment and/or therapy measures may then be applied. The method includes steps of, (a) obtaining a biological sample of the subject;
(b) mixing the biological sample with the monoclonal antibody of the present disclosure so as to react advillin in the biological sample with the monoclonal antibody thereby forming a complex of advillin and the monoclonal antibody in an immunoassay; and
(c) administering an effective amount of a therapeutic agent to the subject to ameliorate the peripheral neuropathy pain, in which the therapeutic agent is a pain reliever, an anti-seizure agent, or an anti-depressant.

According to embodiments of the present disclosure, in the step (a), the biological sample may be any of a whole blood sample, a plasma sample, a serum sample, an ascites (or peritoneal fluid), or a cerebrospinal fluid (CSF) sample, purified or filtered forms thereof, or a skin biopsy. From the view point of early detection, blood, serum, plasma, ascites, CSF, or skin biopsy sample is preferred.

In the step (b), the thus prepared biological samples of the step (a) are then reacted with the monoclonal antibodies of this disclosure via mixing them thoroughly. Formation of the complex of advillin in the biological sample and the present monoclonal antibody is confirmed by conventional ELISA or dot-blot analysis.

In the step (c), an effective amount of a therapeutic agent is administered to the subject to ameliorate the peripheral neuropathy pain. The therapeutic agent may be a pain reliever, an anti-seizure agent, or an anti-depressant. Examples of the pain reliever suitable for use in the present method include, but are not limited to, nonsteroidal anti-inflammatory drugs (NSAIDs) such as aspirin, ibuprofen, dexibuprofen, naproxen, fenoprofen, dexketoprofen, flurbiprofen, loxoprofen, indomethacin, tolmetin, sulindac, etodolac, ketorolac, diclofenac, acelofenac, prioxicam, meloxicam, tenoxicam, droxicam, lornoxicam, isoxicam, phenylbutazone, mefenamic acid, meclofenamic acid, flfenamic acid, and tolfenamic acid: opioids such as tramadol; oxycodone such as oxycotin. Examples of the anti-seizure agent suitable for use in the present method include, but are not limited to, gabapentin and pregabalin. Examples of the anti-depressant suitable for use in the present method include, but are not limited to, amitriptyline, doxepin and nortriptyline.

The present invention will now be described more specifically with reference to the following embodiments, which are provided for the purpose of demonstration rather than limitation.

EXAMPLES

Materials and Methods

Animals

All procedures followed the Guide for the Use of Laboratory Animals (National Academies Press, Washington, DC). The Advillin$^{+/cre}$ mouse line was a kind gift from Dr. Fan Wang (Duke University Medical Center, Durham, NC). Advillin$^{cre/cre}$ mice were used as advillin-KO mice, because advillin exon2 was replaced by a Cre-cassette and homozygous knockin mice do not express any advillin mRNA (Hasegawa H et al., *J Neurosci* (2007) 27(52):14404-14414; Zhou X. et al., *Proc Natl Acad Sci USA* (2007) 107(20): 9424-9429.).

For behavioral studies, Advillin$^{+/cre}$ mice were back-crossed to C57BL/6J mice for 10 generations to establish a congeneric strain. Wild-type mice (WT or Avil$^{+/+}$) and advillin-KO mice (Advillin$^{cre/cre}$ or Avil$^{-/-}$) used in behavioral studies were offspring from heterozygotes (Avil$^{+/-}$) inter-crossed.

For western analysis of CSF samples, C57BL/6J and BALB/cByJNarl mice were used for EAE induction and oxaliplatin treatment. Unless described, adult mice at 8 to 12 weeks old were used in all studies.

Experimental Autoimmune Encephalitis (EAE) Model

For EAE induction, myelin oligodendrocyte glycoprotein peptide (35-55) (product name: MOG$_{35-55}$, MDBio, Taiwan) was emulsified with an equal volume of complete Freund's adjuvant (CFA, Sigma-Aldrich, USA) in PBS. Mice were subcutaneously injected in the hindlimb with the MOG/CFA emulsion (MOG$_{35-55}$ 100 μg/mouse and CFA 400 μg/mouse), followed by two intraperitoneal (i.p.) injections of 200 ng pertussis toxin (List Biological Laboratories, Campbell, CA, USA), on the day of immunization and 2 days later. Clinical scoring was assessed daily and on the days of behavioral test, pathological examination, or CSF collection. The clinical scores were as previously described by Wang I C et al. (*Sci Rep* (2017) 7:42304) with some modification: 0, no clinical signs: 0.5, partially paralyzed tail: 1, tail paralysis: 2, ataxia of lower body: 3, paraparesis of one or both hind limbs: 4, paraplegia of one or both hind limbs: 5, paraplegia of one or both hind limbs with incomplete paralyzed forelimb; 6, death.

Cerebrospinal Fluid (CSF) Collection

Mice were anesthetized with urethane (13% w/v in saline, 1.5-2 mg/g, i.p.), shaved on the neck skin, and mounted on a stereotaxic system (Stoelting, Wood Dale, IL, USA). A sagittal incision inferior to the occiput was made in skin, then subcutaneous tissue and muscles were separated by blunt dissection with forceps. The pulled glass capillaries were used to puncture cisterna magna through the dura mater. Approximately 6 μl CSF was collected per mouse, then immediately frozen in tubes on dry ice and transferred to a −80° C. freezer. All CSF samples used for western blotting showed no visible contamination of blood.

Preparation of Rabbit Polyclonal Antibody Against Mouse Advillin

A peptide "DGEPKYYPVEVLKGQNQEL" (SEQ ID NO: 3) corresponding to the headpiece domain of mouse advillin was synthesized and conjugated with ovalbumin. The synthetic peptides were given to rabbits to boost the generation of polyclonal antibodies of advillin. Sera were collected and purified with columns coupled with corresponding antigen. For immunostaining of cutaneous tissue, the advillin antibody was absorbed with 0.5% (w/v) acetone powder of advillin-KO mouse livers to minimize non-specific binding.

Western Blot Analysis

Primary antibodies used in western blot were rabbit polyclonal anti-mouse advillin (1 µg/ml), mouse monoclonal anti-human advillin, and rabbit anti-albumin (1:1000, both GeneTex, San Antonio, TX, USA). Mouse DRGs, mouse spinal cords, and human 293T cells (ATCC CRL-3216) were collected, and protein was extracted with RIPA buffer supplied with proteinase inhibitor (Roche, Switzerland). Cerebrospinal fluid (CSF) samples or protein from cell lysates separated by SDS-PAGE were transferred onto PVDF membranes by using a Mini Trans-Blot Electrophoretic Transfer Cell (Bio-rad, CA, USA). The membranes were blocked with 5% milk in TBST (1×TBS with 0.1% TWEEN® 20 from Sigma-Aldrich) for 1.5 hr at room temperature and incubated with the primary antibody for 1.5 hr at room temperature. Then the membranes were washed three times for 10 min each with TBST and incubated with the appropriate secondary antibody (1:10000, GeneTex):goat anti-rabbit IgG (H+L) horseradish peroxidase (HRP) and goat anti-mouse IgG (H+L) HRP. All antibodies were diluted in blocking solution. Enhanced chemiluminescence (ECL) involved the Immobilon ECL Kit (Millipore, MA, USA) and signals were detected by using the BioSpectrum Auto Imaging System (UVP, CA, USA). For detecting advillin in CSF samples, ECL involved the SuperSignal West Femto ECL kit (Thermo Fisher Scientific, PA, USA)

Plasmid Construction

The full-length cDNA of human advillin (GenBank accession no. NM_006576) obtained from human placenta cDNA was cloned into pGEM-T easy vector (Promega, USA). The PCR cloning involved the forward primer 5'-gagggatc-catgcctctgaccagtgccttca-3' (SEQ ID NO: 36) and reverse primer with stop codon 5'-cgctctagacttgctttagaaaagcccctt-3' (SEQ ID NO: 37). Advillin cDNA was subcloned into p3×FLAG®-CMV14 expression vector (Sigma).

Cell Culture and Transfection

HEK293T cells were maintained in DMEM (Invitrogen, CA, USA) supplemented with penicillin (100 U/mL)/streptomycin (100 µg/mL) (Invitrogen) and 10% (v/v) fetal bovine serum (FBS, Invitrogen). For transfection of plasmids, HEK293T cells at >90% confluence were transfected with lipofectamine 2000 (Invitrogen). The primary culture of DRG neurons was conducted in accordance with the process described by Cheng C M. et al. (*Nat Protoc* (2010) 5(4):714-724). Briefly, total DRG of mice (6-12 weeks old) were dissected and collected for two-step digestion: first, 0.125% type I collagenase (Sigma) in HBSS (Invitrogen) for 60 min at 37° C.; second, 0.125% trypsin (Invitrogen) in HBSS for 20 min at 37° C. The fully digested DRG cells were washed with DMEM (Invitrogen) containing 10% (v/v) FBS, then triturated and plated on coverslips coated with poly-L-lysine (PLL) and laminin (both Sigma). Cells were cultured with DMEM containing 10% (v/v) FBS and penicillin (100 U/mL)/streptomycin (100 µg/mL) and maintained under 5% $CO_2$ at 37° C.

Pain Behavior

Cold allodynia was assessed by the cold plate test with an innocuous temperature (Toyama S. et al. (2014) *Anesthesiology* 120(2):459-473). The temperature of the cold plate (35100, Ugo Basile, Milan, Italy) was set at 15° C. and was allowed to stabilize for 5 min. The mouse was then placed onto the cold plate and contained within a clear Plexiglas chamber at 3.5 cm height to prevent the mouse from standing. The behavior was recorded for 150 sec. Nocifensive behaviors were assessed by counting the events of flicking, shaking, licking, flinching, guarding, lifting the forepaws, and licking the hind paws, and body jumping or shaking during the recording period. Also, the latency to the first nocifensive responses was determined. The oxaliplatin-administered mice (15 mg/kg, i.p.) were recorded before drug injection as the baseline and at post-day 2, 4, and 12. The experimenters for counting nocifensive behaviors were blinded to the mouse genotypes.

CCI-Decompression Model

The chronic constriction injury (CCI) model was as previously described (Tseng T J, et al. (2008) *Exp Neurol* 204(2):574-582: Lorenz J E, et al. (2014) *Antioxid Redox Signal* 21(10):1504-1515). Briefly, mice were anesthetized with 2% isoflurane. The left sciatic nerve was exposed at mid-thigh level and loosely ligated with 6-0 silk sutures in three ligatures separated by a 1-mm distance. The incision of skin was then stitched by using 5-0 silk sutures. At day 14 after sciatic nerve constriction, mice were anesthetized and underwent a decompression procedure by carefully removing all the loose ligatures.

Immunohistochemistry Assay and Image Quantification

Adult mice (8-12 weeks old) with or without CCI surgery were anesthetized with urethane (13% w/v in saline, 1.5-2 mg/g, i.p.), perfused via the cardiac vascular system with normal saline and then 4% paraformaldehyde (Sigma) fixative in 0.1M PBS (pH=7.4). Spinal cords were collected, post-fixed at 4° C. overnight, cryoprotected with 30% sucrose overnight, and frozen with OCT (Leica, Germany) for cryosectioning. Cryosectioned tissues were stored in −80° C. before use. Sections were washed with TBST (TBS with 0.1% TWEEN® 20) and incubated with blocking solution (5% BSA, 0.1% tritonX-100 in TBS) at room temperature for 1 hr. The primary antibody goat anti-CGRP (Serotec, UK), advillin and Alexa Fluor-conjugated secondary antibodies (Invitrogen) were diluted in blocking solution. Sections were incubated with primary antibodies at 4° C. overnight, washed three times with TBST, then incubated with secondary antibodies at room temperature for 90 min. After a wash, sections were mounted with Vectashield mounting medium (Vector Laboratories, CA, USA). The immunohistochemistry images were obtained by LSM 700 confocal microscope (Carl Zeiss, Germany). The immunoreactivity of advillin in the spinal-cord dorsal horn was measured by using ImageJ. After background subtraction, the ratio of ipsilateral to contralateral dorsal horn was calculated.

Preparation of Human Monoclonal Antibody of Advillin

For the preparation of immunogen, the synthetic peptide "KNQNQELPEDVNPAKKENYLSE" (SEQ ID NO: 1) corresponding to the headpiece domain of human advillin was appended with amino acid "cysteine" in N terminal and conjugated to carrier ovalbumin. The Balb/c mice were used for immunization, applied with the primary injection (0.1 mg antigen and complete adjuvant) and booster injections (0.1 mg antigen and incomplete adjuvant). After the verification of polyclonal serum, the final booster (0.05 mg antigen) was performed, then the hybridoma cells were created, sub-cloned by limiting dilution, and screened by use of another synthetic peptide "LKNQNQELPEDVNPAKKE- NYLSEQD" (SEQ ID NO: 2) via ELISA. The validated clones were certified with the expression plasmid of human advillin via western blot.

Components and respective nucleic acid and amino acid sequences of the present human advillin monoclonal antibody are summarized in Tables 1 and 2.

TABLE 1

Sequences of the heavy chain of anti-advillin antibody

| Name | Nucleic Acid Sequence (SEQ ID NO) | Amino Acid Sequence (SEQ ID NO) |
| --- | --- | --- |
| Leader sequence | 4 | 20 |
| Framework region (FR)1 | 5 | 21 |
| CDR1 | 6 | 22 |
| FR2 | 7 | 23 |
| CDR2 | 8 | 24 |
| FR3 | 9 | 25 |
| CDR3 | 10 | 26 |
| FR4 | 11 | 27 |

TABLE 2

Sequences of the light chain of anti-advillin antibody

| Name | Nucleic Acid Sequence (SEQ ID NO) | Amino Acid Sequence (SEQ ID NO) |
| --- | --- | --- |
| Leader sequence | 12 | 28 |
| FR1 | 13 | 29 |
| CDR1 | 14 | 30 |
| FR2 | 15 | 31 |
| CDR2 | 16 | 32 |
| FR3 | 17 | 33 |
| CDR3 | 18 | 34 |
| FR4 | 19 | 35 |

Example 1. Advillin as a Biomarker for the Detection of Peripheral Neuropathy 1.1 Advillin is Present in CSF of EAE Mice Inventors' previous studies found that advillin located in growth cones of neurite during axonal regeneration, and advillin-associated nascent focal-adhesion protein complex often "shed-off" after neurite retraction in cultured DRG neurons. Thus, it was hypothesized that nerve damage on isolectin B4+ (IB4+) sensory axons (i.e., peripheral neuropathy) might cause advillin-associated nascent focal-adhesion protein shed-off from growth cones, eventually be detected in CSF or plasma.

To prove such hypothesis, the well-established mouse model of multiple sclerosis that shows severe peripheral neuropathy associated with IB4$^+$ sensory neurons—experimental autoimmune encephalomyelitis (EAE) mouse model, was employed. EAE model was established and EAE-induced symptoms in mice were evaluated by the paralysis degree of tails and limbs and used as clinical scores of disease severity and reflecting the degree of nerve damage in accordance with procedures described in the "Materials and Methods" section. CSF of naïve mice and EAE mice were respectively collected and analyzed for the presence of advillin by western blot.

As expected, advillin protein was detectable in CSF of EAE mice in the recovery phase, defined as after day 30 in the EAE model, high proportionally with a clinical score ≥3. However, advillin was hardly detectable in naïve healthy mice (FIG. 1). Quantified results are summarized in Table 1.

Table 1. Quantification of western blot analysis of advillin expression in CSF from naïve mice and EAE mice.

TABLE 1

Quantification of western blot analysis of advillin expression in CSF from naïve mice and EAE mice.

| | EAE score | Sample no. | Avil+ |
| --- | --- | --- | --- |
| Naïve | 0 | 5 | 0 |
| KO | 0-3 | 5 | 0 |
| EAE | 0-2 | 18 | 6 |
| | 3-4 | 9 | 6 |

The result in this example confirmed our hypothesis that peripheral neuropathy will cause advillin-associated nascent focal-adhesion protein shed-off from growth cones, eventually be detected in CSF of the injured subject.

1.2 Advillin is Present in CSF of Animals Subjected to Chemotherapy Induced Cold Allodynia To mimic chemotherapy induced neuropathy pain, a single dose of oxaliplatin (15 mg/kg, i.p.) was administered to test animals to induce cold allodynia, latency to the first nocifensive sign were then recorded. CSF from both naïve mice and oxaliplatin-induced cold allodynia mice were respectively collected and analyzed for the presence of advillin by western blot.

Figure 2:
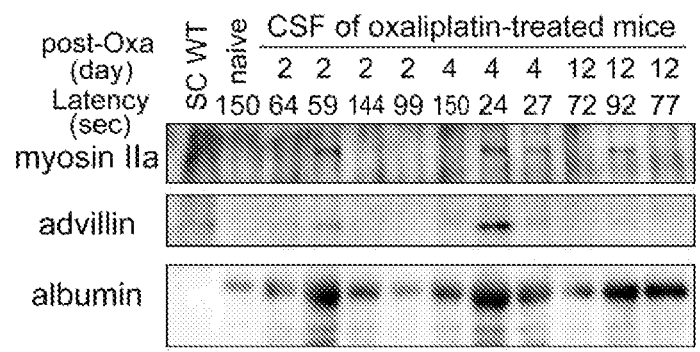
FIG. 2 Advillin in the CSF of oxaliplatin-treated mice. (A) A representative Western blot for detection of advillin protein in the CSF of oxaliplatin-treated mice. Each lane was loaded with 5 μl CSF sample or 10 μg WT spinal cord lysates as a positive control. Albumin was a loading control. The sample-collecting time post-oxaliplatin treatment is shown. The latency of nocifensive response is used as an index of severity of neuropathic pain. Myosin IIa is an advillin-interacting protein. SC WT is the spinal cord cell lysate from WT mice. (B) Quantification of advillin expression in CSF samples. The dotted line is the threshold level (mean of negative samples+5×SD) to define the positive advillin expression. The early phase is defined as day to day 7 after oxaliplatin treatment and the late phase as ≥ day 8.
Figure 2:
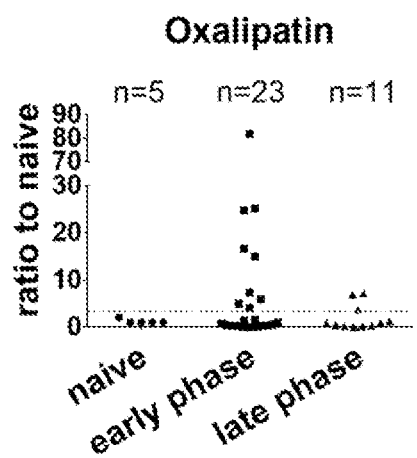

Similar to finding in example 1.1, advillin was detected in mice exhibiting short latency (<65 sec) to cold stimulation at 2 or 4 days post-oxaliplatin treatment, whereas advillin was not detected in mice with long latency to cold stimulation (FIG. 2).

1.3 Advillin is not Present in CSF of Animals Subjected to Complete Freund's Adjuvant (CFA) Induced Inflammatory Pain To confirm advillin is a biomarker for peripheral neuropathy pain only, complete Freund's complete adjuvant (CFA) was injected into test animals to cause inflammatory pain. CSF was then collected from each of these animals and analyzed for the presence of advillin. For the purpose of comparison, CSF from oxaliplatin-treated animals (e.g., animals of example 1.2) were also collected and analyzed.

Figure 3:
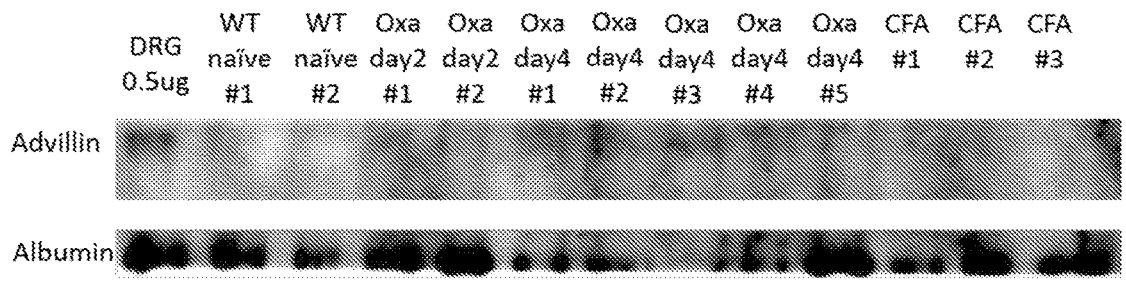
FIG. 3 Advillin protein in the CSF of oxaliplatin-treated or CFA-treated mice. Each lane was loaded with 4 μl CSF sample or 0.5 μg DRG lysate as a positive control. Albumin was a loading control. Advillin was detected in the CSF samples of oxaliplatin-treated mice but not in the CFA-treated mice.

As illustrated in FIG. 3, advillin was not detected in CSF of animals suffering from CFA-induced inflammatory pain.

1.4 Advillin is Present in CSF of Animals Subjected to Chronic Constriction Injury of the Sciatic Nerve In this example, mice that model severe neuropathic pain associated with local nerve injury from compression of sciatic nerve were used to verify if advillin contributed to such pain. Briefly, sciatic nerves of the mice were surgically ligated (or compressed) to produce chronic constriction injury (CCI). At 14 days after CCI, surgical decompression was performed, in which the ligatures on sciatic nerves were removed. CSFs in CCI mice and control mice were collected, and analyzed for the presence of advillin by western blot.

Figure 4:
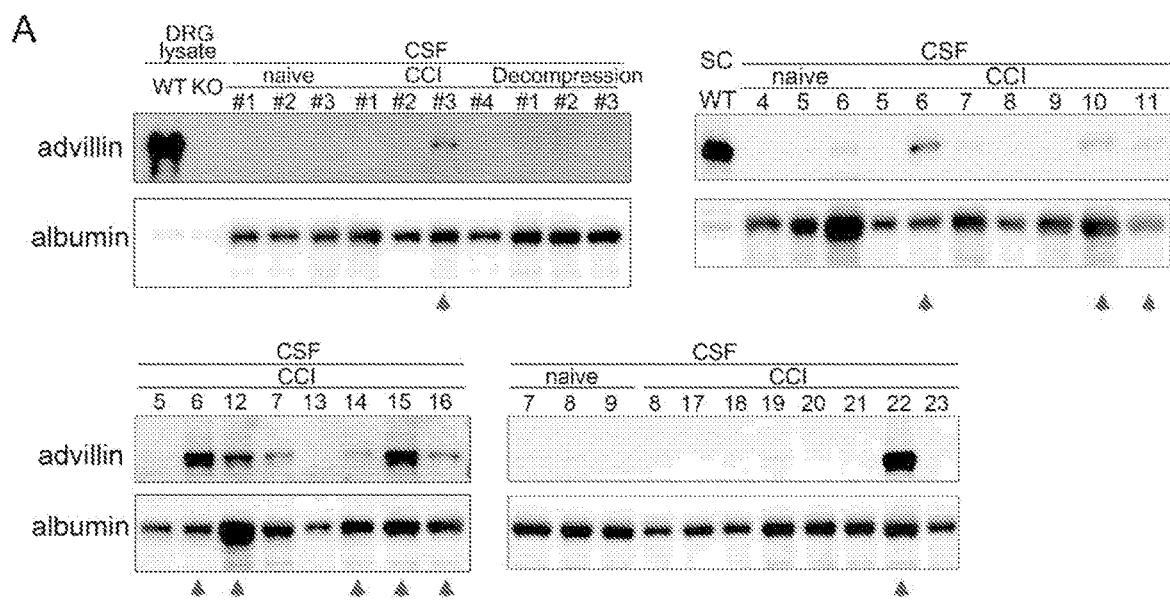
FIG. 4 Advillin protein in the CSF of mice treated with chronic constriction injury (CCI) of the sciatic nerve. (A) Western blot analysis of advillin protein level in CSF of CCI mice. CSF samples were collected from naïve, CCI (postoperative day 7, 8, 9, and 10), and decompression mice. Each lane was loaded with 6 μl CSF sample or 0.5 μg DRG lysate or 10 μg WT spinal cord lysate (SC WT). WT DRG and WT SC were used as positive control. KO DRG was used as negative control. Arrow heads indicated positive samples. (B) Quantification of advillin expression in CSF samples. The dotted line is the threshold level (mean of naïve samples+5×SD) to define the positive advillin expression.
Figure 4:
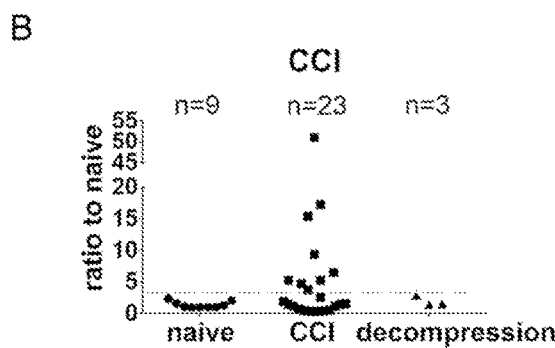

As the data depicted in FIG. 4, advillin was detected in CCI mice, but not in CCI-decompression mice.

Figure 5:
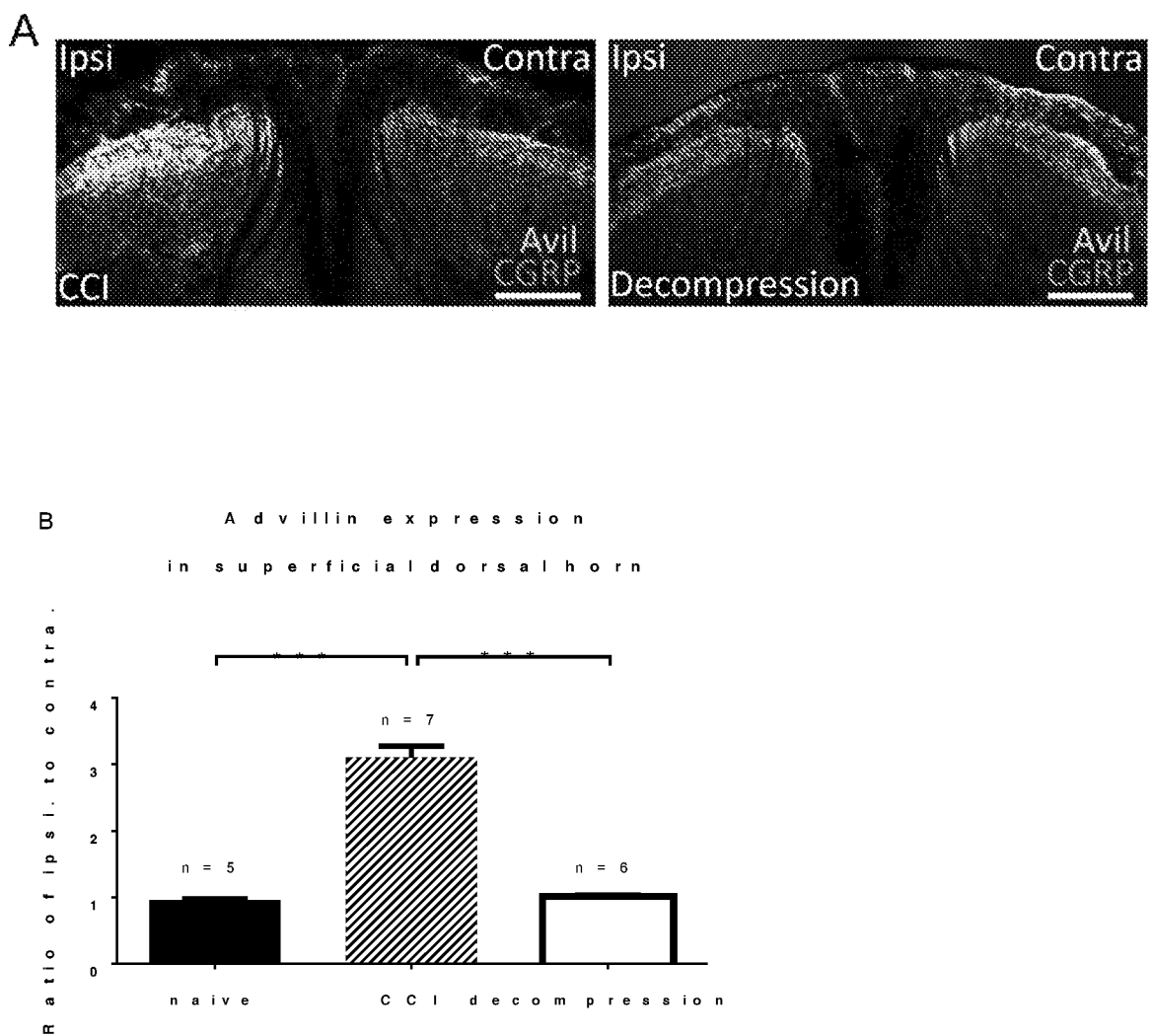
FIG. 5 CCI-induced up-regulation of advillin in the spinal cord dorsal horn. (A) Advillin immunoreactivity in the spinal cord dorsal horn was significantly increased in the ipsilateral side of CCI mice (at postoperative day 9) as compared with naïve and CCI-decompression mice. (Scale bars: 200 μm.) (B) Quantification of advillin immunoreactive intensity in superficial dorsal horns is shown and analyzed with one-way ANOVA. ****$P<0.0001$.

In addition, advillin distribution in naïve, CCI and CCI-decompression mice were also determined. As illustrated in FIG. 5, sciatic nerve compression significantly increased the expression of advillin in the ipsilateral dorsal horn on day 9, which then returned to normal basal level of naïve mice 2 weeks after decompression.

Taken together of data presented in examples 1.1, 1.2, 1.3, and 1.4, advillin may serve as a specific biomarker for diagnosis of peripheral neuropathy pain.

Figure 6:
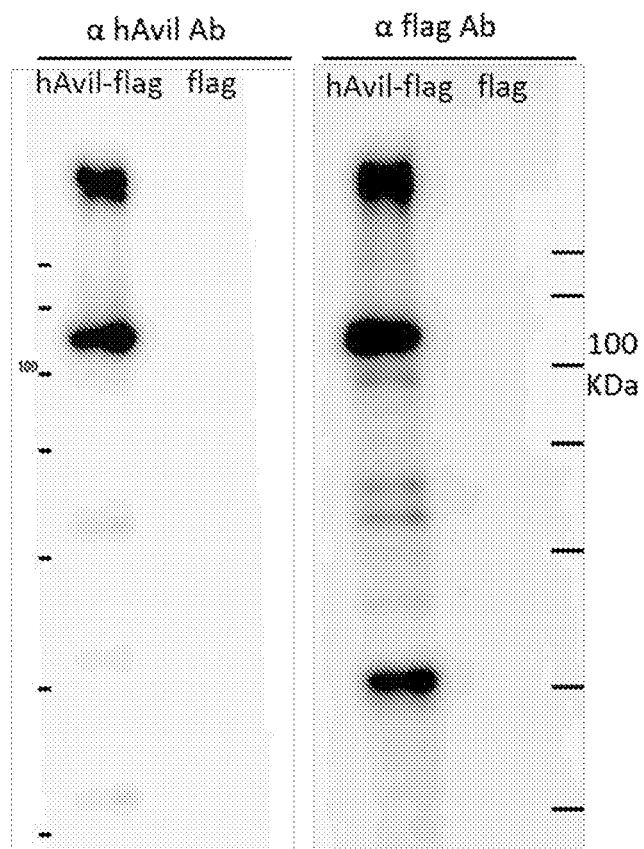
FIG. 6 The monoclonal antibody of human advillin specifically recognized exogenous expression of human advillin in 293 cells. Human advillin clone was tagged with FLAG®, and the construct of human advillin-FLAG® (hAvil-FLAG®) or vector control (FLAG®) were transfected into 293 cells. The lysates were detected with the monoclonal antibody of human advillin and FLAG® antibody respectively. The molecular weight of human advillin is predicted as 92 KDa and the detected signals were corresponded to predicted size of hAvil-FLAG® around 100 KDa. The top signal is supposed as aggregated forms as detected in the FLAG®-antibody recognized signal.
Figure 7:
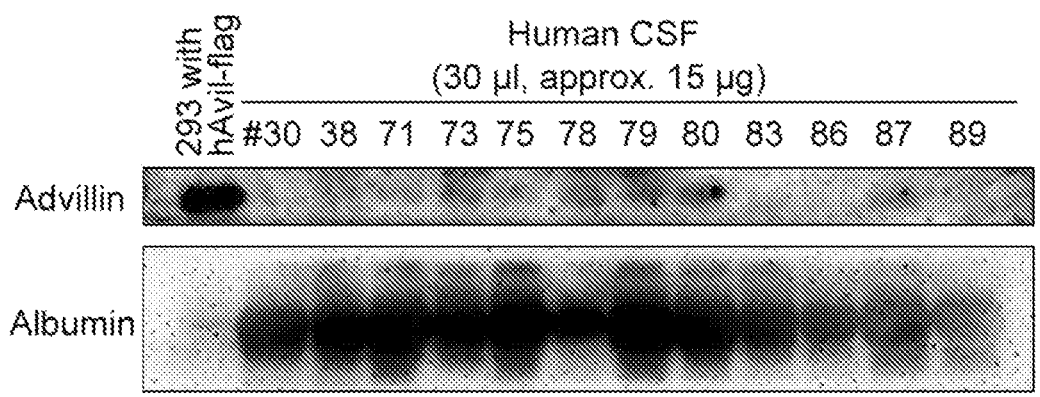
FIG. 7 The monoclonal antibody hAvil can detect the advillin expression in human CSF of patients treated with oxaliplatin. The CSF samples of patients underwent chemotherapy with oxaliplatin were collected. Each lane was loaded with 30 μl CSF sample (approximate 15 μg) or 2 μg cell lysate of 293 cell transfected with hAvil-FLAG® as a positive control. Albumin was a loading control of CSF. CSF #73, 78, 79 and 80 were samples with apparent signals (above threshold).

Example 2. Confirmation of the Specificity of Monoclonal Antibody of Human Advillin To achieve specific measurement for human samples, monoclonal antibodies for human advillin (hereafter "hAvil") were generated in accordance with procedures described in the "Materials and Methods" section. The specificity of hAvil was verified by binding with exogenous expression of human advillin clone (FIG. 6). Further, hAvil could specifically detect advillin in human CSF collected from patients treated with oxaliplatin (FIG. 7).

The data confirmed that the hAvil is highly specific for human advillin and is suitable for clinical detection of advillin present in CSF collected from subjects suffering from peripheral neuropathy pain.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A monoclonal antibody that specifically binds to an epitope of advillin comprising,
    a heavy chain variable region comprising a heavy chain complementarity-determining region 1 (HCDR1), a HCDR2, and a HCDR3 having the amino acid sequences of SEQ ID NOs: 22, 24, and 26, respectively; and
    a light chain variable region comprising a light chain complementarity-determining region 1 (LCDR1), a LCDR2, and a LCDR3 having the amino acid sequences of SEQ ID NOS: 30, 32, and 34, respectively.

2. The monoclonal antibody of claim 1, wherein the antibody is an IgG or an IgM.

3. A kit comprising the monoclonal antibody of claim 1 and a legend indicating how to use the kit.

* * * * *